(12) United States Patent
Ollivier et al.

(10) Patent No.: US 9,067,058 B2
(45) Date of Patent: Jun. 30, 2015

(54) NANO MULTIPOLE RINGS FOR MEDICAL MICROLEADS

(71) Applicant: SORIN CRM S.A.S., Clamart (FR)

(72) Inventors: Jean-François Ollivier, Villiers le Bâcle (FR); Nicolas Shan, Juvisy sur Orge (FR); Philippe D'Hiver, Châtillon (FR)

(73) Assignee: SORIN CRM S.A.S., Clamart (FR)

( * ) Notice: Subject to any disclaimer, the term of this patent is extended or adjusted under 35 U.S.C. 154(b) by 0 days.

(21) Appl. No.: 13/916,444

(22) Filed: Jun. 12, 2013

(65) Prior Publication Data

US 2013/0338745 A1    Dec. 19, 2013

(30) Foreign Application Priority Data

Jun. 13, 2012    (FR) .................... 12 55544

(51) Int. Cl.
*A61N 1/05* (2006.01)
*H01R 4/24* (2006.01)

(52) U.S. Cl.
CPC . *A61N 1/05* (2013.01); *A61N 1/056* (2013.01); *H01R 4/2491* (2013.01)

(58) Field of Classification Search
USPC ............................................ 607/116
See application file for complete search history.

(56) References Cited

U.S. PATENT DOCUMENTS

| 4,387,727 | A | 6/1983 | Sandstrom |
|---|---|---|---|
| 4,590,950 | A | 5/1986 | Iwaszkiewicz et al. |
| 5,370,684 | A | 12/1994 | Vallana et al. |
| 5,387,247 | A | 2/1995 | Vallana et al. |
| 7,364,479 | B1 | 4/2008 | Deily |
| 2005/0030765 | A1* | 2/2005 | Southard et al. ............. 362/559 |
| 2008/0114230 | A1 | 5/2008 | Addis |
| 2008/0177343 | A1 | 7/2008 | Dal Molin et al. |
| 2010/0331934 | A1 | 12/2010 | McDonald et al. |
| 2012/0130464 | A1 | 5/2012 | Ollivier |

FOREIGN PATENT DOCUMENTS

| EP | 2 455 131 | 5/2012 |
|---|---|---|
| EP | 1 983 881 | 6/2013 |

OTHER PUBLICATIONS

Preliminary Search Report for French Patent Application No. 1255544, dated Sep. 11, 2012, 2 pages.

* cited by examiner

*Primary Examiner* — Joseph Dietrich
(74) *Attorney, Agent, or Firm* — Foley & Lardner LLP

(57) ABSTRACT

One embodiment of the invention relates to a multipolar lead for implantation in a venous, arterial, or lymphatic network, and for use with an electric stimulation or detection device. The invention includes at least two microcables, each having a central conductor for connection to the electric stimulation or detection device. The invention further includes a first ring having at least two lumens, each sized to receive a microcable of the at least two microcables, wherein one of the at least two lumens is a connection lumen which receives a first microcable of the at least two microcables. The ring further includes a connection element movable into the connection lumen to pierce a sheath of the first microcable and to press into the central conductor of the first microcable received by the connection lumen, electrically connecting at least a portion of the first ring to the central conductor.

16 Claims, 9 Drawing Sheets

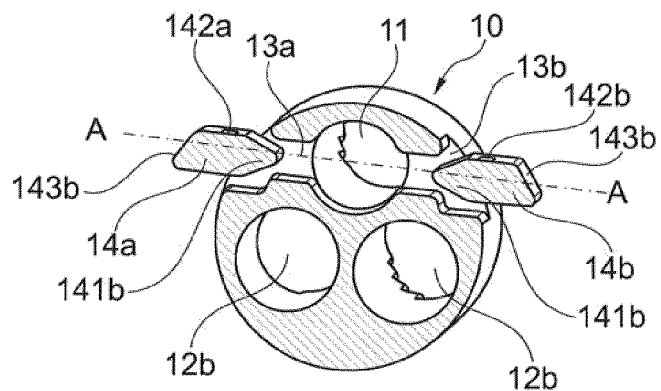
Fig. 1a
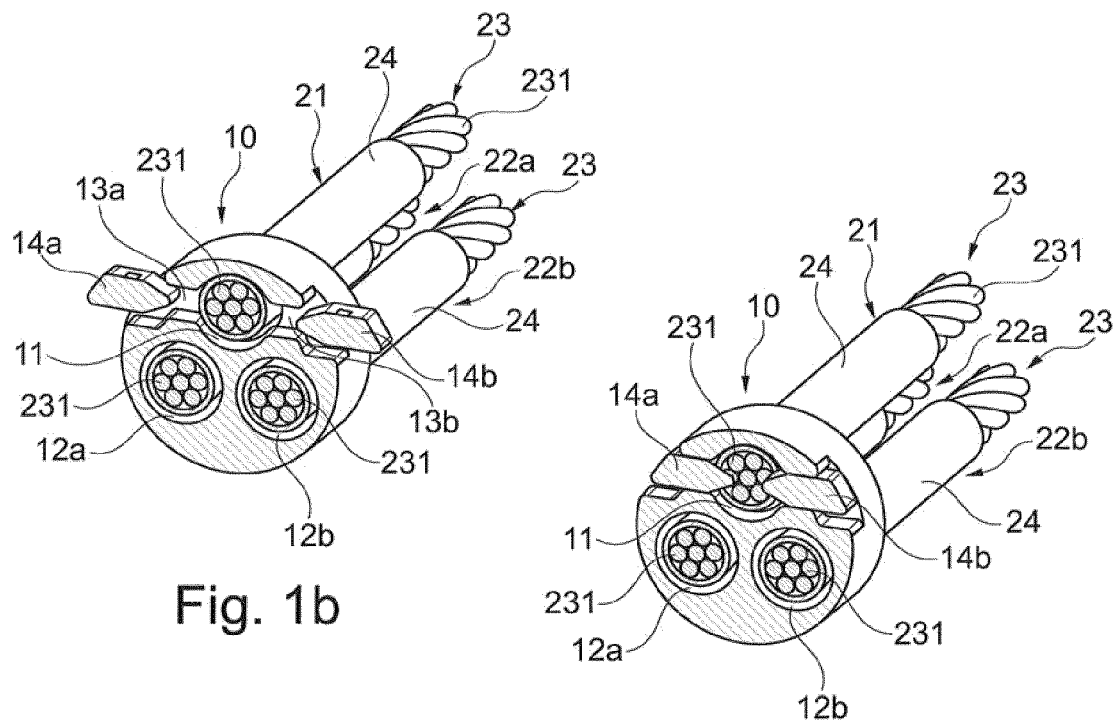
Fig. 1b
Fig. 1c

NANO MULTIPOLE RINGS FOR MEDICAL MICROLEADS

CROSS REFERENCE TO RELATED APPLICATIONS

This application claims the benefit of and priority to French Patent Application No. 1255544, filed Jun. 13, 2012, the entirety of which is incorporated by reference.

BACKGROUND

The invention relates generally to the "active implantable medical devices" field as defined by Directive 90/385/EEC of 20 Jun. 1990 the Council of the European Communities. The invention more specifically relates to a detection and/or stimulation microlead intended to be implanted in venous, arterial or lymphatic networks, and to deliver an electrical pulse and/or to detect an electrical activity. Such a lead can be used in cardiology and, for example, can be implanted in the coronary sinus vein to stimulate a left or right cavity of the heart. Microleads are also useful in many other medical applications. For example, microleads can be used whenever there is a venous, arterial or even lymphatic network, including the venous or arterial cerebral network. Electrical stimulation led to major advances in neurology in the field of neuromodulation, a technique which includes stimulating target areas of the brain for the treatment of disorders such as Parkinson's disease, epilepsy and other neurological diseases. Such a technique can advantageously provide a less invasive approach.

A continuing challenge in many microlead applications is to reach areas which are relatively inaccessible due to small size constraints. Some stimulation "microleads" are therefore of very small diameter but are also extremely robust to ensure the long-term biostability.

The size of some current implantable leads is on the order of 4 to 6 French (1.33 to 2 mm). It would be desirable to reduce the diameter to less than 2 French (0.66 mm). Such a size of microlead would reach very small veinlets, inaccessible today with some types of larger devices. It is challenging to provide microleads of such small size which are also able to easily navigate through the venous arterial or lymphatic networks with sufficient flexibility to be introduced into vessel networks with high tortuosity, anastomosis, etc. The reduction in lead diameter increases microlead technological complexity, imposes technical constraints, and generates technical risks.

Some leads include a microcable having a central conductor for connection to an electrical generator. The conductor may be coated with an electrically insulating sheath. One or more sensing/pacing electrodes may be electrically connected to the central conductor, and are intended to come into contact with the wall of the target vessel.

One technique for producing electrodes of such leads is described in EP 2455131 A1 and its US counterpart US2012/0130464 (Sorin CRM SAS). This technique includes locally stripping the insulation to expose the microcable in one or more points. The stripped points together form a network of electrodes connected in series to provide the stimulation points and thus ensure multizone dissemination of the stimulation energy delivered by the implant. The same document also proposes an alternative embodiment in which the working portion of the microlead is provided by successively and alternately threading on the microcable insulating tubes and short conductive electrodes of platinum-iridium. The insulating tubes, made for example of polyurethane, are affixed to the microcable and the platinum-iridium electrodes are crimped directly to the microcable. Another technique includes applying a coating of the microcable of insulating polyurethane adhesive, leaving some uncoated conductive surfaces.

With these techniques, which include the exposure of microcable (removal of the insulating surfaces or surfaces left in reserve), it is desirable to provide a conductive coating, such as an alloy of titanium nitride or a carbon deposit such as Carbofilm by a cathode sputtering technique such as described in particular in U.S. Pat. No. 5,370,684 A and U.S. Pat. No. 5,387,247 (Sorin Biomedica SpA), to protect from corrosion the exposed cable. The conductive coating may be made of an alloy such as MP35N (35% Ni, 35% Co, 20% Cr and 10% Mo). However, such a material is relatively sensitive to electrocorrosion, a corrosion phenomenon accentuated by the current flow in the polar regions (electrodes) and by contact with surrounding body fluids (blood, etc.).

In some applications it may be desirable to avoid any risk of infusion of corporeal fluids to the microcable. The microcable may thus be completely isolated from any contact with the environment of the microlead. This can be provided by an additional conductive coating of titanium nitride NiTi or carbon on the electrode areas or crimping platinum-iridium rings (noble material, resistant to corrosion) on the microcable.

Long life duration is a key parameter which must be taken into account when designing a stimulation microlead. Indeed, the heart beats and movement of organs can induce significant bending strains. In particular, a stimulation microlead by the venous system may be locally deformed under curvatures much higher than those experienced by a conventional lead, since it must follow the deformation of the veins.

French patent application FR 12 54548 of May, 16, 2012, titled "Structure of electrode for a detection/stimulation monopolar microlead intended to be implanted in a cardiac or brain vessel" proposes to produce the detection/stimulation electrode in the form of a metal ring crimped onto the microcable. The inner face of the ring is in mechanical and electrical connection with the microcable surface in at least one perforation region of the sheath. However, at the periphery, the inner face of the ring is in mechanical connection with the surface of the sheath. In other words, insulating material of the sheath is positioned between the microcable and the ring in regions on both sides the perforation area of the sheath. An advantage of such electrodes is that they do not require stripping the microcable to electrically connect to the central conductor. Such electrodes also do not require a special conductive coating or NiTi carbon.

In some applications, however, it is desirable to have a multipolar lead. A multipolar lead can provide for bipolar stimulation by delivering pulses between two electrodes located at the end of a lead, or between two electrodes of a right ventricular lead. This stands in contrast to stimulation between an electrode (or a series of electrodes) and the housing of the generator, such as with many monopolar lead.

Another advantage of the multipolar leads is the possibility to implement an "electronic repositioning." This feature allows a surgeon to select, from the various electrodes present on the lead, the electrode which provides the best compromise between prevention of phrenic nerve stimulation, electrical efficiency and hemodynamic effectiveness. Such a multiple electrode lead is in particular described in EP 1983881 A1 and its US counterpart US2008/0177343 (Sorin CRM S.A.S.). In this method, it is possible to direct or redirect the electric field between the different electrodes arranged along the pacing lead of the left cavity and/or with the electrodes of the pacing lead of the right ventricle. This technology allows managing micro-displacements and changes in the hemodynamic behavior (reverse modelling) simply by reprogramming the generator by telemetry through the skin, without heavy reoperation. U.S. 2008/0114230 A1 and U.S. Pat. No. 7,364,479 B1 describe exemplary electrode supporting structures for such a multipolar lead.

In the case of a multipolar lead, the presence of a plurality of conductors (typically three conductors) disposed along the lead body renders conventional crimping of a ring-shaped electrode as impractical, because such conventional crimping would likely indiscriminately perforate the conductors of the lead.

SUMMARY

An object of the invention includes providing a multipolar lead with multiple microcables. The invention may provide for a relatively reliable mechanical and electrical connection between conductors and electrodes, and may advantageously provide for physical continuity of microcables. The invention may provide for increased mechanical strength of the conductors by providing intermediate supportive components inserted between different portions of the microcables. The invention may provide for good sealing around the surfaces of the microcables to avoid exposing them to bodily fluids. According to some exemplary embodiments, the invention provides an external lead diameter typically of 1 to 2 French (0.33 to 0.66 mm). Some embodiments of the invention can provide relatively high flexibility and thus can maintain a high degree of trackability.

According to some embodiments of the invention, a multipolar detection/stimulation lead is intended to be implanted in a venous, arterial or lymphatic network. The lead body itself may be as shown and described in U.S. 2008/0114230 A1 cited above. The lead body may include, for example, at least two microcables, each having a full central conductor intended to be connected to the generator of an active implantable medical device. The lead may further include a sheath of an insulating polymeric material surrounding the central conductor on its periphery and along its length. The lead may further include at least one detection/stimulation electrode intended to be electrically connected to a central conductor of a microcable and to come against a wall of a target vessel of said venous, arterial or lymphatic network. The lead may further include an electrical connection between the electrode and a central conductor. The outer diameter of the lead may be at most equal to 2 French (0.66 mm). The electrode may be provided by a cylindrical metal ring having a longitudinal lumen for electrical connection adapted to receive a microcable to be connected to the ring.

The electrode further may further include an electrical connection formed by perforating the sheath. The perforation may be provided by at least one transverse guiding tunnel to the ring, formed between the periphery of the ring and the lumen for electrical connection. An electrical connection drawer slides in the guiding tunnel and has an inner end shaped to penetrate the sheath of the microcable present in the lumen to make electrical contact between the ring and the central conductor of the microcable.

According to an exemplary embodiment of the invention, the lead according to the invention is multipolar; it has a plurality of microcables whose number depends mainly on the number of intended poles. These microcables are inserted through lumens arranged on a plurality of metal rings arranged along the lead and forming electrodes. Each ring includes a connection lumen receiving a microcable. The connection lumen is configured to electrically connect the ring to the central conductor. The other lumens allow their respective microcables to pass through without forming an electrical connection. The electrical connection between the microcable to be connected and the metal ring may be performed by a connection drawer (e.g., member, piercing element, etc.), the force sliding movement of which in the guiding tunnel causes perforation of the insulating sheath of the microcable by the inner end of the drawer.

The technique of electrical connection by perforation provides for quality sealing around the microcables and aids in their protection against electrocorrosion (e.g., without the need to use a conductive coating of NiTi or carbon). In addition, the physical continuity of the microcables is improved, giving the entire lead excellent mechanical strength even under high curvature, e.g. at the crossing of high tortuosity vessels and anastomosis.

In one exemplary embodiment providing for improved sheath perforation, the axis of sliding of the connection drawer passes through the center of the connection lumen. The lead may further include two opposite connection drawers. Furthermore, in order to avoid the formation on the periphery of the metal ring of protrusions which would affect the isodiametric profile of the lead, the connection drawer in the perforation position (e.g., closed) is fully retracted into the guiding tunnel.

It is possible that the lumen crossing the electrode receives a plurality of microcables not connected to the ring. The lead may include, at the periphery of the ring, at least one area of non-crossing longitudinal grooves. In this method, effects of peak are created generating a better transmission of electrical pulses to the tissues.

To avoid discontinuities in the insulation of the lead assembly, the lead may include a collective outer sheath of heat shrinkable insulating material, windows being cut in this sheath around detection/stimulation surfaces of the ring, which further may carry longitudinal grooves. According to other advantageous optional embodiments, a seal of flexible adhesive may be deposited at the ends of the ring, and a chamfer or a recess is arranged at each ring end, in particular in order to best manage the ring/body lead stiffness gradient.

Some embodiments of the invention relate to an electrode structure for a monopolar detection/stimulation microlead to be implanted in a cardiac or cerebral vessel. This lead, the diameter of which may be at most equal to 2 French (0.66 mm) (in some embodiments) includes several microcables (21, 22a, 22b) each with a full central conductor (23) and an insulating sheath (24). The electrode is formed of a metal ring (10) having a longitudinal connection lumen (11) receiving a microcable (21) intended to be connected to the ring, and longitudinal electrode crossing lumens (12a, 12b) of receiving the microcables (22a, 22b) not connected to the ring. The conductive ring is connected to the conductor of the microcable by perforation of the sheath (24) surrounding this conductor, with a connection drawer (14a, 14b) sliding in a transverse guiding tunnel (13a, 13b) and perforating the microcable sheath so as to make electrical contact through the connection drawer mounted and clamped in the guiding tunnel.

One embodiment of the invention relates to a multipolar lead for detection/stimulation for implantation in a venous, arterial or lymphatic network. The multipolar lead includes at least two microcables (21, 22a, 22b). Each of the microcables may include a full central conductor (23) intended to be connected to a generator of active implantable medical device, and a sheath (24) of an insulating polymeric material surrounding the central conductor on its periphery and along its length. The lead can further includet least one detection/ stimulation electrode intended to be electrically connected to a central conductor (23) of a microcable (21) and to come against a wall of a target vessel of said venous, arterial or lymphatic network. The lead can further include a drawer for electrical connection between the electrode and a central conductor. The external diameter of the lead may be at most equal to 2 French (0.66 mm). The at least one electrode may be a cylindrical metal ring (10) having a longitudinal lumen (11) for electrical connection adapted to receive a microcable (21) intended to be connected to the ring, and at least one longitudinal lumen (12a, 12b) for electrode crossing (e.g., passing through without forming an electrical connection). The longitudinal lumen (12a, 12b) for electrode crossing is adapted to receive at least one microcable (22a, 22b) not connected to the ring. Said at least one electrode further includes capabilities for electrical connection by perforation including at least one guiding tunnel (13a, 13b) transverse to the ring, formed between the periphery of the ring and the lumen for electrical connection, and an electrical connection drawer (14a, 14b) sliding in the guiding tunnel and having an inner end (141a, 141b) conformed to penetrate the sheath (24) of the microcable present in the connection lumen in order to make electrical contact between the ring and the central conductor of this microcable via the connection drawer mounted and clamped in the guiding tunnel.

In an exemplary embodiment, the axis (AA) of sliding of the connection drawer passes through the center of the connection lumen. In an exemplary embodiment, the ring includes two opposed connection drawers. In one embodiment, in a perforation position, the connection drawer is fully retracted into the guiding tunnel. The inner end of the connection drawer may have a protruding shape. The connection lumen has a circular opening of a diameter equal to the diameter of the microcable connected to the ring. The at least one electrode crossing lumen may have a circular opening of a diameter greater than the diameter of the microcable not connected to the ring. There may be an additional protection insulating sheath inserted in said at least one electrode crossing lumen. The circular opening of said at least one electrode crossing lumen may have, in a central zone of the ring, a diameter equal to the diameter of the circular opening of the connection lumen. The at least one electrode crossing lumen may receive a plurality of microcables not connected to the ring. The lead may include at least one zone (144) of temporary connection between the connection drawer and the ring (10). The lead may further include, on the periphery of the ring, at least one zone (18a, 18b, 18c) with non-crossing longitudinal grooves (181). The radius of the longitudinal grooves is at least equal to 5 μm.

The lead may be covered with a collective outer sheath (30) in a heat-shrinkable insulating material, windows (31) being cut in the sheath around detection/stimulation surfaces (18a, 18b, 18c) of the ring. The detection/stimulation surfaces may include with longitudinal grooves (181). A seal of flexible adhesive (40) may be placed in the ring ends. The flexible adhesive may be made of polyurethane. A chamfer (16a, 16b) may be arranged at each end of the ring. A recess (17) may be arranged at each end of the ring. The recess may be tangent to the lumens of the ring. The electrical connection may include a connection punch (14) cut into the ring. The electrical connection may include a perforation member (14') combined with the ring in the same mastering section, the perforation member and the ring being made of two materials of different stiffness. The electrical connection may include a single movable connection element (14", 14'") of the fork type. The connection element (14'") may include a clip system in the connection lumen.

One embodiment of the invention relates to a multipolar lead for implantation in a venous, arterial, or lymphatic network, and for use with an electric stimulation or detection device. The invention includes at least two microcables, each having a central conductor for connection to the electric stimulation or detection device. The invention further includes a first ring having at least two lumens, each sized to receive a microcable of the at least two microcables, wherein one of the at least two lumens is a connection lumen which receives a first microcable of the at least two microcables. The ring further includes a connection element movable into the connection lumen to pierce a sheath of the first microcable and to press into the central conductor of the first microcable received by the connection lumen, electrically connecting at least a portion of the first ring to the central conductor. The multipolar lead can further include a second ring having at least two lumens including a pass through lumen configured to receive the first microcable and a second connection lumen configured to receive a second microcable of the at least two microcables; wherein the second connection lumen pierces a sheath of the second microcable to electrically connect at least a portion of the second ring to the second microcable. The first microcable is connected to a first port of the electric stimulation or detection device and wherein the second microcable is connected to a second port of the electric stimulation or detection device.

BRIEF DESCRIPTION OF THE FIGURES

FIG. 1a is a perspective cross-sectional view of a metal ring forming a multipolar lead electrode, according to an exemplary embodiment.

FIG. 1b shows the ring of FIG. 1a with three microcables.

FIG. 1c shows the ring of FIG. 1b in a puncture position of a microcable.

FIG. 2b is a perspective view of the ring shown in FIG. 2a.

FIG. 7b is a perspective view of the ring shown in FIG. 7a.

FIG. 9b is a detail view of FIG. 9a.

DETAILED DESCRIPTION

Figure 2A:
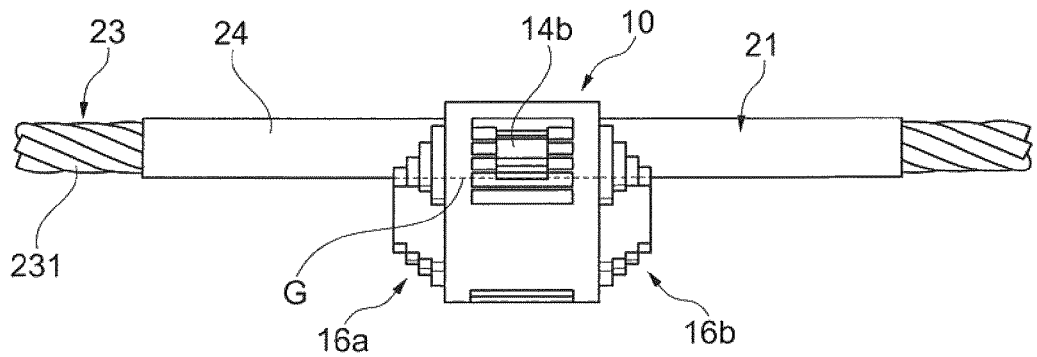
FIG. 2a is a side view of a metal ring with two chamfered ends.

Referring now to the Figures, embodiments providing for electrodes of multipolar leads are shown and described.

In FIGS. 1a, 1b and 1c, a cylindrical metal ring 10 forms a sensing/pacing electrode for a multipolar lead. In the illustrations of FIGS. 1b and 1c, the ring 10 receives three microcables 21, 22a and 22b. In other exemplary embodiments, the number of microcables is three or four. The electrode provided by the ring 10 is intended to be electrically connected to one of the microcables and to come into contact with a wall of a target vessel of the venous, arterial or lymphatic system. The ring 10 may be made of a material resistant to the electrocorrosion phenomenon such as an alloy of platinum-iridium (typically 90/10) or of another noble metal, such as palladium or tantalum.

The cylindrical metal ring 10 can have a diameter substantially equal to 1 to 2 French (0.33 to 0.66 mm). The ring is shown to include three longitudinal lumens 11, 12a and 12b extending in parallel to the axis of the ring 10. One of these lumens, the lumen 11, in FIGS. 1a-1c, receives the microcable 21 and is intended to be electrically connected to the ring 10 and thus to a pole of the generator.

It should be noted that, in alternative embodiments, the microcable is locally stripped prior to any crimping activity, providing for mechanical and electrical contact between the connection lumen of the ring and the active microcable without perforation of the insulation.

Longitudinal lumens 12a and 12b may be considered "crossing lumens" in so far as they allow microcables 22a and 22b, which are not to be connected to the ring 10, to cross the ring.

As shown in FIGS. 1a-1c, the connection lumen 11 has a circular opening of a diameter substantially equal to that of the microcable 21. Conversely, the crossing lumens 12a and 12b may have a diameter greater than that microcables 22a and 22b, in order to avoid any risk of damage to the insulation of microcables adjacent to the ring. This increase in diameter can also allow for easy insertion of additional insulation surrounding those microcables, allowing an intentional increase in microcable stiffness adjacent the ring.

In other embodiments, the crossing lumens 12a, 12b have a diameter substantially equal to that of the connection lumen 11. This can advantageously provide for centering of the unconnected microcables 22a and 22b. An area of greater diameter 15 is shown more particularly on the detail view of FIG. 9b. It is also possible to replace the individual electrode crossing lumens 12a and 12b with a single large lumen (not shown) adapted to receive a plurality of unconnected microcables. Such a lumen may for example have a curved oblong shape.

It should be noted that some alternative embodiments may include two to four independent or redundant lines, with two lines being assigned to a single group of electrodes.

In the illustrated version with three lines, it may be possible to assign different specific functions to the third microcable if the generator has only one bipolar connection port (connection of the IS1 type). Such functions may include connection redundancy with a series of electrodes, radiopacity through a section of strands of radiopaque material, for example mainly in PtIr, pure mechanical strength in tension and bending, with a section for example mainly of MP35NLT.

Microcables 21, 22a and 22b are shown as formed of a full central conductor 23 surrounded by a sheath 24 of insulating polymeric material.

The central conductor 23 is shown as a multi-stranded structure in the form of a strand of a plurality of conductor strands 231 of small diameter. Typically, one central conductor has seven strands 231 of 33 μm in diameter for a total diameter of 100 μm. According to an exemplary embodiment, a strand 231 has a bi-material structure, namely a core in Platinium and a stainless sheath of an alloy such as MP35 N (35% Ni, 35% Co, 20% Cr and 10% Mo) or MP35 NLT, having an advantage of fatigue endurance. The reduction in diameter of the individual strands can reduce the stress applied to each of them, and therefore can increase the fatigue performance of the structure of the strand. Such a structure, without internal lumen and with several strands twisted together, is advantageously capable of both endurance against cardiac movements and resistance to stress-related implantation.

As an additional precaution, the MP35N can be coated with platinum to ensure full protection of the electrical junction against the electrocorrosion. This may help protect the device if the seal at the puncture through the insulation or between the connection drawer and the guiding tunnel, or even the seal of the possible gluing, is not stable.

Regarding the insulating sheath 24, it should meet the following requirements: fatigue resistance, electrical isolation, long-term biocompatibility, biostability, transformation possibility and compatibility with the central conductor 23. The materials that can be used in this context include the materials of the group comprising: polyurethanes (PU), polyesters (PET), polyamides (PA), polycarbonates (PC), polyimides, fluorinated polymers, polyether ether-ketone (PEEK), poly-p-xylylene (parylene) and polymethyl methacrylate (PMMA). Materials are that of high chemical inertness such as fluoropolymers, which also have very good insulation. Among these compounds, mention may be made of materials of the group consisting of: polytetrafluoroethylene (PTFE), FEP (perfluorinated propylene), PFA (copolymer resin perfluoroalkoxy), HSR (tetrafluoroethylene, hexafluoropropylene, vinylidene fluoride), PVDF (polyvinylidene fluoride), the EFEP (ethylene fluorinated ethylene propylene) and ETFE (ethylene tetrafluoroethylene). The methods for making the sheath insulation 24 on the central conductor 23 may be a function of the materials used, for example coextrusion of the conductor (for PU, PA, PEEK, polyimide and fluoropolymers) deposition by immersion in a solution (PU, PA and polyimides), heating of a heat shrinkable tube (for PET and fluoropolymers), chemical deposition using a gas (for parylene), plasma processing to improve adhesion between the layers. Although the invention has been illustrated with a single layer of the same material sheathing the microcables 21, 22a and 22b, it is possible to provide several layers forming the sleeve 24, e.g. a layer of PET and a layer of ETFE.

In an exemplary embodiment, the insulating sheath 24 has a typical thickness of 5 to 20 μm.

As shown in FIGS. 1a, 1b and 1c, the electrical connection between the ring 10 and the microcable 21 is made by perforation of the insulating sheath 24 of the microcable 21. The perforation is shown to be made with two transverse metal connection drawers 14a, 14b, each equipped with an inner end 141a, 141b conformed (i.e., positioned, sized, etc.) to perforate the sheath 21 of the microcable present in connection lumen 11, so as to make electrical contact between the ring 10 and the central conductor 23 of the microcable 21 via the drawers 14a, 14b.

The connection drawers 14a, 14b include an inner end 141a, 141b of projecting shape and can slide in respective guiding tunnels 13a, 13b transverse to the ring 10, provided between the periphery of the ring and the connection lumen 11.

To prevent the formation of projections outside of the periphery of the ring 10, the connection drawers 14a, 14b, in perforating position, are preferably retracted fully within the respective guiding tunnels 13a, 13b.

The fit between a connection drawer and the associated guiding tunnel is intended to be tight enough: (a) to establish the electrical connection between the drawer and the ring 10; (b) to maintain the drawer in the closed position (on this point, it is possible to develop projections 142a, 142b in the drawers 14a, 14b to locate and better control the mechanical interference); and (c) to prevent the infiltration of body fluids to the strands of the microcable 21, to prevent the risk of corrosion.

In practice, the perforation of the insulating sheath 24 of the microcable 21 is completed by force provided by crimping jaws on the surfaces 143a and 143b of the connection drawers 14a, 14b.

The system with two-opposed connection drawers allows reliable microcable/ring connection, on the one hand, by a "pincer effect" on the microcable receiving opposite connection pressure and, secondly, by the redundancy of the contact on the microcable.

In an exemplary embodiment, the opposed connection drawers 14a, 14b slide in the tunnels 13a, 13b, along the same sliding axis AA, and through the center of the connection lumen 11. The sliding of the drawers 14a, 14b guide the thrust surfaces 143a, 143b perpendicular to the movement of the crimping jaws. An alternative solution is to make parallel the thrust surfaces of the connection drawers to use crimping equipment with parallel and non-concentric jaws.

Figure 5:
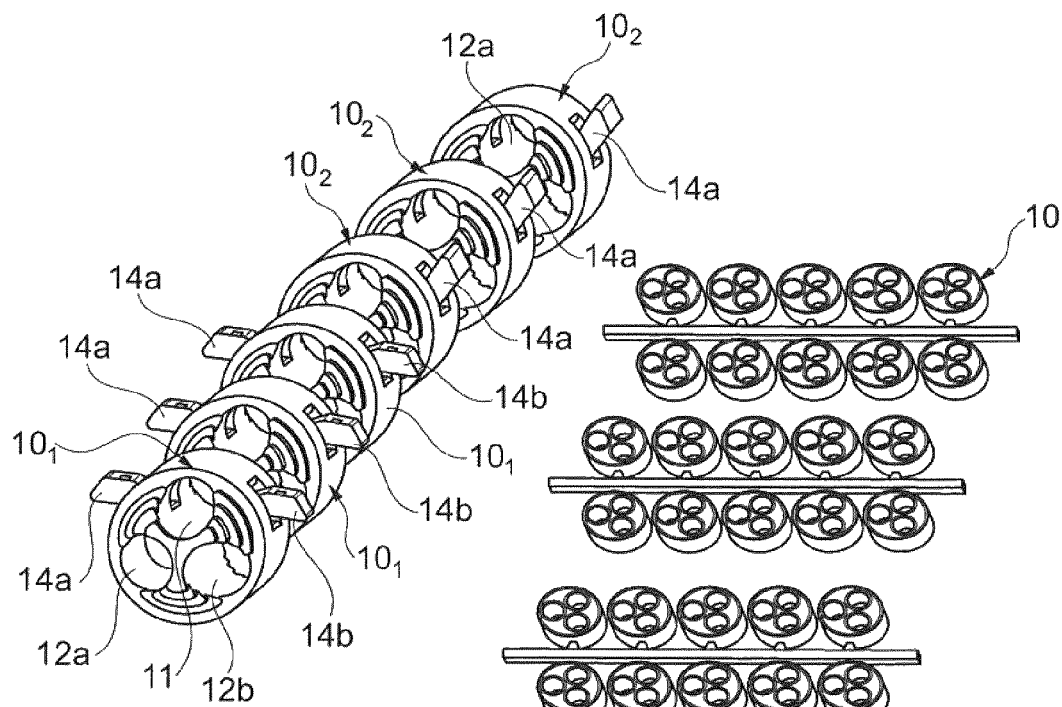
FIG. 5 is a perspective view of a plurality of metal rings constituting the electrodes of a multipolar lead.

FIG. 5 shows an element of a multipolar lead including six rings, the first three $10_1$ are connected to a same microcable, while the last three $10_2$ are connected to another microcable (due to a different orientation of the rings). The choice of the connected microcable to a given electrode is determined by the angular positioning of the ring in the pre-assembly of the lead as a whole. To reduce risk of incorrect mounting, the angular sequence of stacking of rings can be encoded on the assembly tool, the keying being obtained from the fact that the protruding zone of the connection drawers 14a, 14b must enter in a notch formed on the tool.

Figure 6:
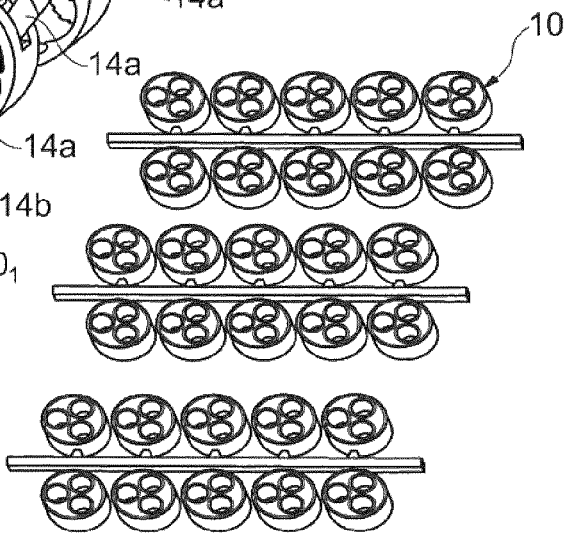
FIG. 6 shows clusters of metal rings arranged to make multipolar leads according to the invention.

The alternative solution of FIG. 6 is to stack the clusters of rings one on top of the other, the position of each ring 10 on a cluster being determined by the choice of the microcable to be connected. The alignment of the lumens allows the simultaneous introduction in a single step of the microcables through all the rings, the latter being then detached from the cluster. It then remains to longitudinally position the rings prior to the crimping operation.

During the insertion of the microcables, the protruding inner ends 141a, 141b for perforation of the connection drawers 14a, 14b are completely retracted inside guiding tunnels 13a, 13b, thus avoiding introduction difficulties of the microcables since the connection lumens 11 are totally free.

Figure 4A:
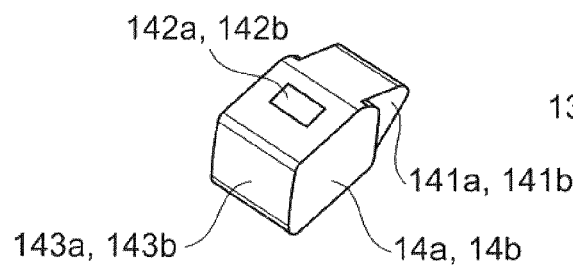
FIG. 4a is a perspective view of a connection drawer.
Figure 4B:
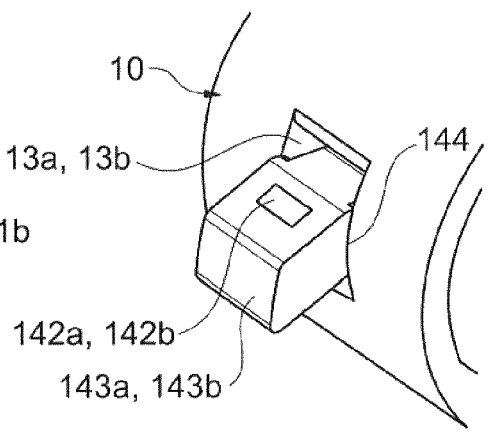
FIG. 4b shows the connection drawer of FIG. 4a in position a guiding tunnel.

One or more temporary attachment areas, such as the zone 144 of FIG. 4b, are provided in the axial direction for example. These areas are intended to keep the drawers 14a, 14b in the open position during all manufacturing operations of the rings, of inspection and assembly of the cables to the crimping step. Under the force of the jaws, the temporary attachment areas are broken and no longer hinder the sliding movement of the drawers in the guiding tunnels 13a, 13b.

One can notice that the concentric crimping operation, the move of which is controlled, does not require angular tracking of the assembly. In addition, a quick visual inspection and/or final inspection of production allows identification of the state of the system, namely "connected" state for electrodes without protuberance, or "not connected" state for electrodes with one or two protuberances.

One method of making of the rings 10 is the MICA Freeform (registered trademark of Microfabrica, Inc.) process for its specificities: extreme precision, integration of components, etc. With this technology by successive layers, the metal ring 10, the connection drawers 14a, 14b and the temporary attachment zones 144 form one piece.

Figure 7A:
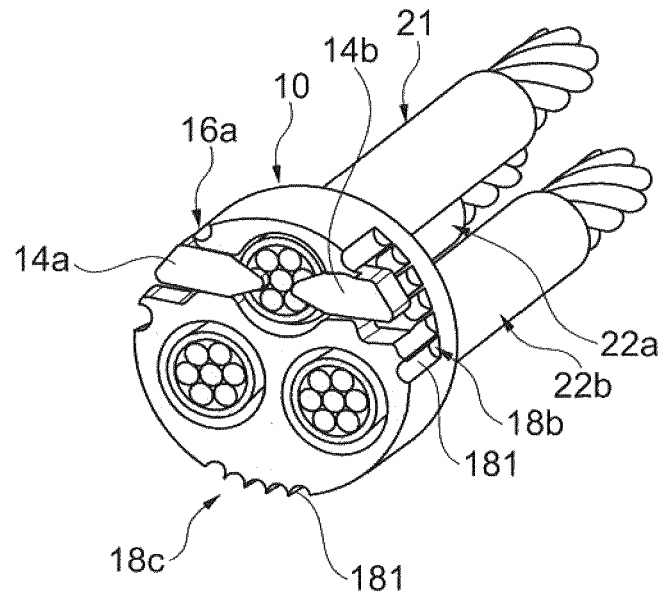
FIG. 7a is a perspective sectional view of a metal ring with longitudinal grooves.
Figure 7B:
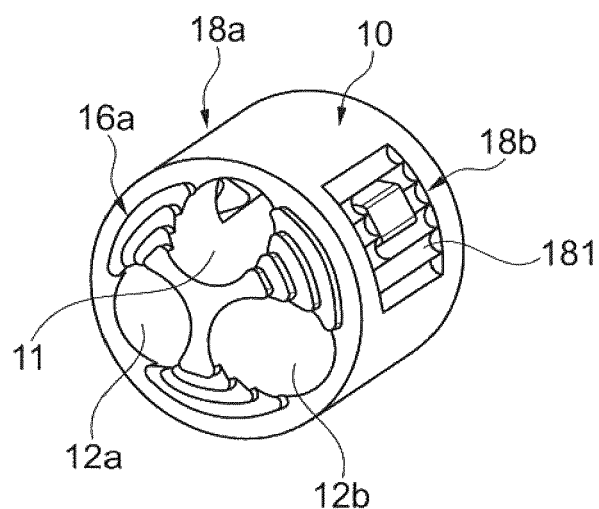

In order to improve by peak effect transmission of the electrical pulses to the target tissue, it is provided on the periphery of the ring 10 areas, referenced 18a, 18b and 18c in FIGS. 7a and 7b, with flush longitudinal grooves 181 contained within the surface of the ring.

Figure 8A:
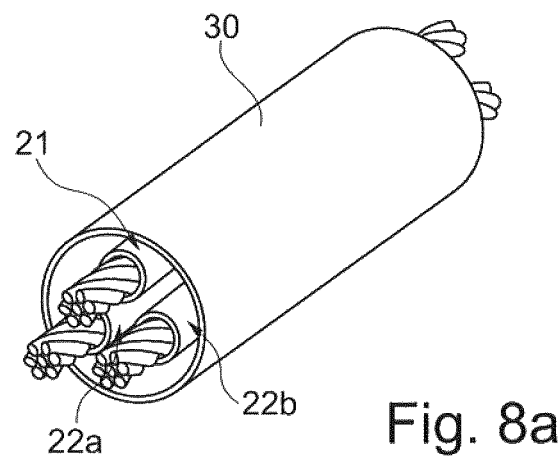
FIG. 8a is a perspective view of a multipolar lead element surrounded by a heat shrink collective sheath.
Figure 8B:
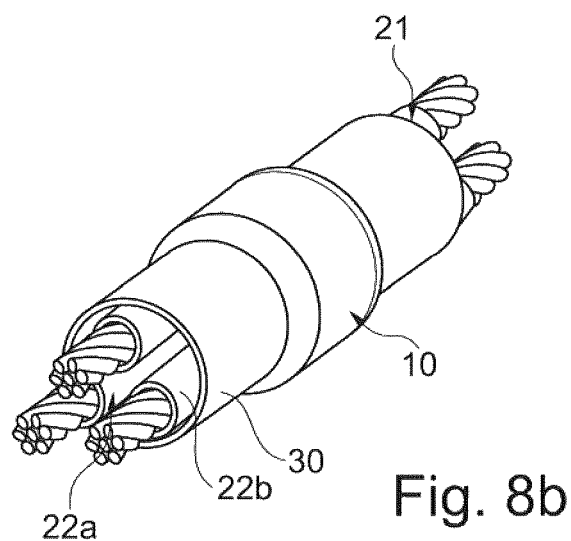
FIG. 8b shows the lead element of FIG. 8a after heating of the heat shrink sheath.
Figure 8C:
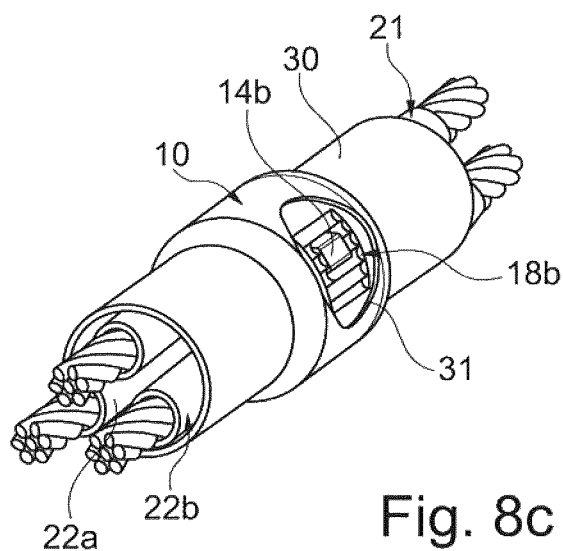
FIG. 8c shows the lead element of FIG. 8b provided with detection/stimulation surfaces.

These grooves 181, with a radius at least equal to 5 μm, are not crossing to maintain at each end of the cylindrical ring 10 a perimeter which ensures the longitudinal sealing function of the electrode during the application of a heat shrink collective sheath 30 shown in FIGS. 8a, 8b and 8c.

This collective sheath 30 prevents any discontinuity of the overall isolation and the creation of local stiffness gradients. Windows 31 are cut into the collective sheath 30 (e.g., by laser ablation) around surfaces of stimulation, namely here the zones 18a, 18b and 18c of the longitudinal groove. Only those groove areas in contact with tissue are pacing zones.

Figure 2B:
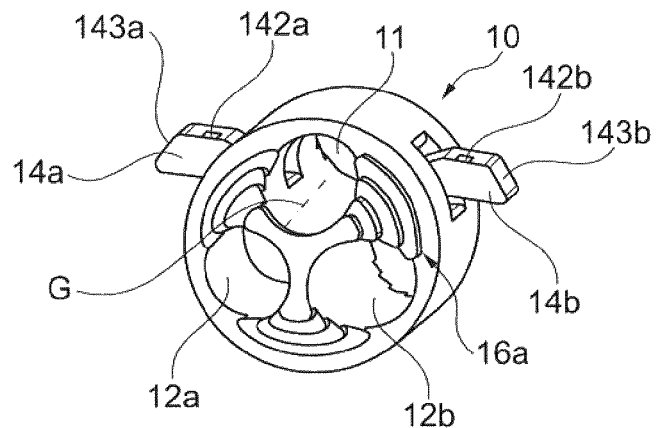
Figure 3:
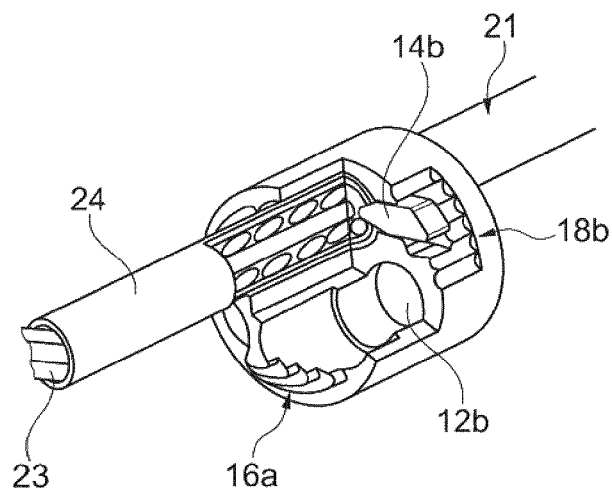
FIG. 3 is an exploded view of the ring of FIGS. 2a and 2b.

In FIGS. 2a, 2b and 3, a metal ring 10 provided at each end with a chamfer 16a, 16b is shown. This characteristic has the advantage of protecting the insulating sheaths 24 of the microcables of abrasive contact with the outer edge of the ring. Indeed, under the action of the heat-shrinkable sheath 30, the three microcables can be held in position in their respective lumen over a length corresponding to the largest generatrix G of the connection lumen 11 shown in FIGS. 2a and 2b. These chamfers also allow better management of the ring/lead body stiffness gradient. The chamfers 16a, 16b may be made in the same time as the ring 10 according to MICA Freeform technology, which gives them the stepped profile that can be observed in the figures above.

Figure 10A:
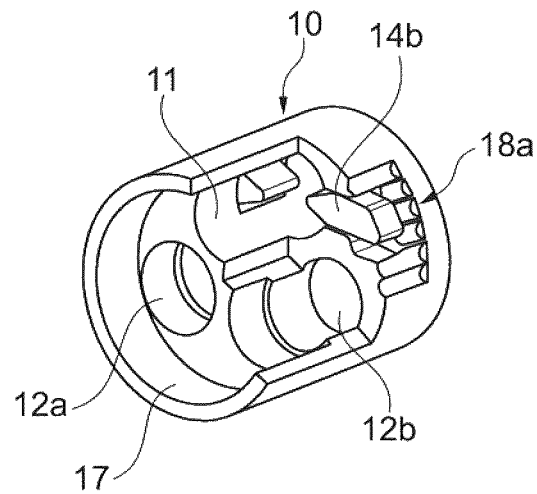
FIG. 10a is an exploded perspective view of a ring with an end counterbore.
Figure 10B:
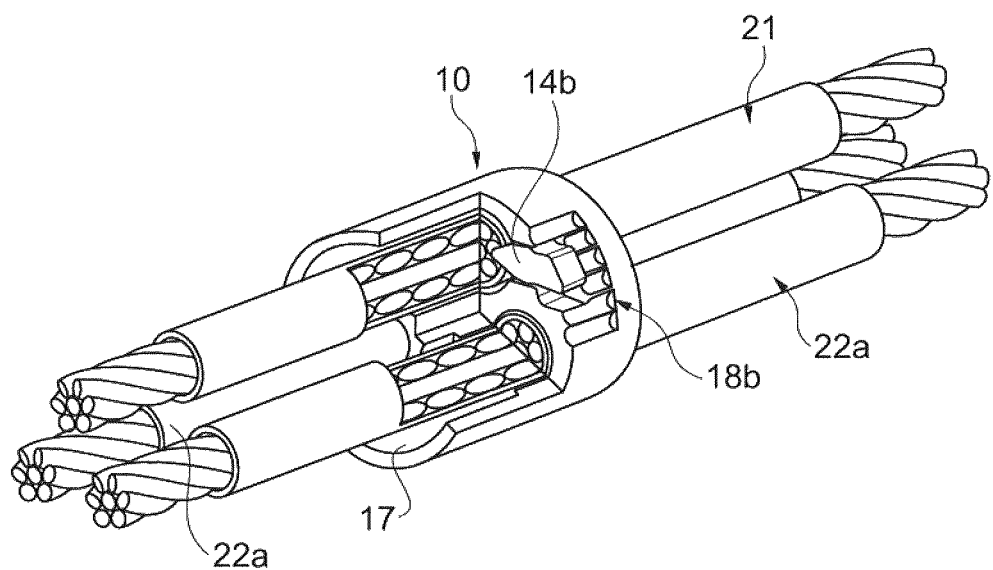
FIG. 10b shows the ring of FIG. 10a equipped with microcables.
Figure 11A:
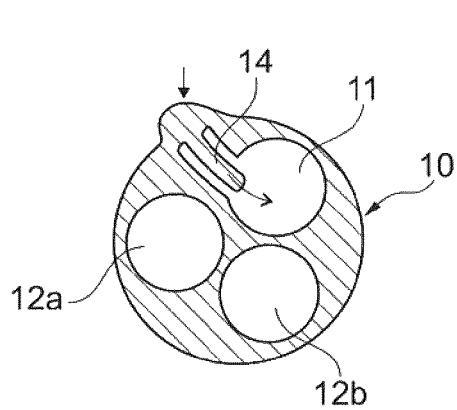
FIGS. 11a to 11c and 12a to 12b are sectional views of alternative embodiments of the metal ring.
Figure 11B:
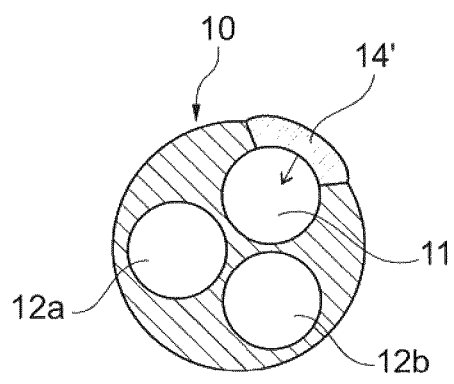
Figure 11C:
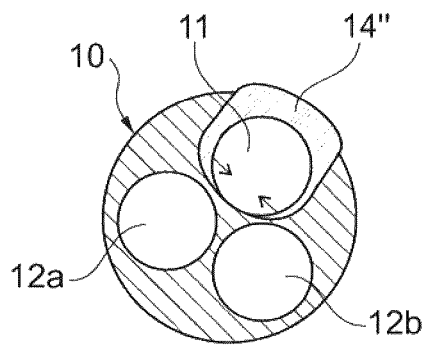
Figure 12A:
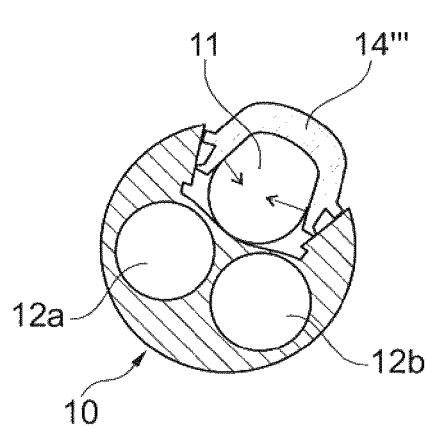
Figure 12B:
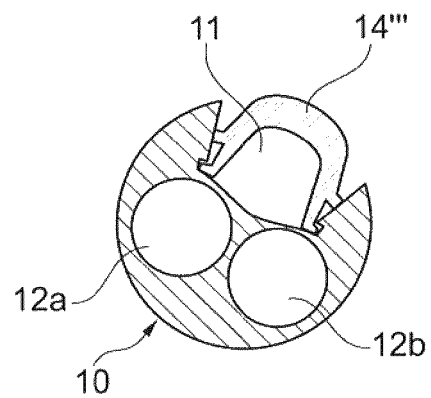

To enable the microcables to abut against a hard surface along one of their outside generatrix, it is possible, as shown in FIGS. 10a and 10b, to develop a counterbore 17 common to each end of the ring 10. Preferably, the counterbore 17 is tangent to the three lumens 11, 12a and 12b. This avoids too sporadic contact against the rim of the ring 10, which could concentrate stress at a point of the insulating sheath 24 of the microcables and locally weaken the sheath.

Figure 9A:
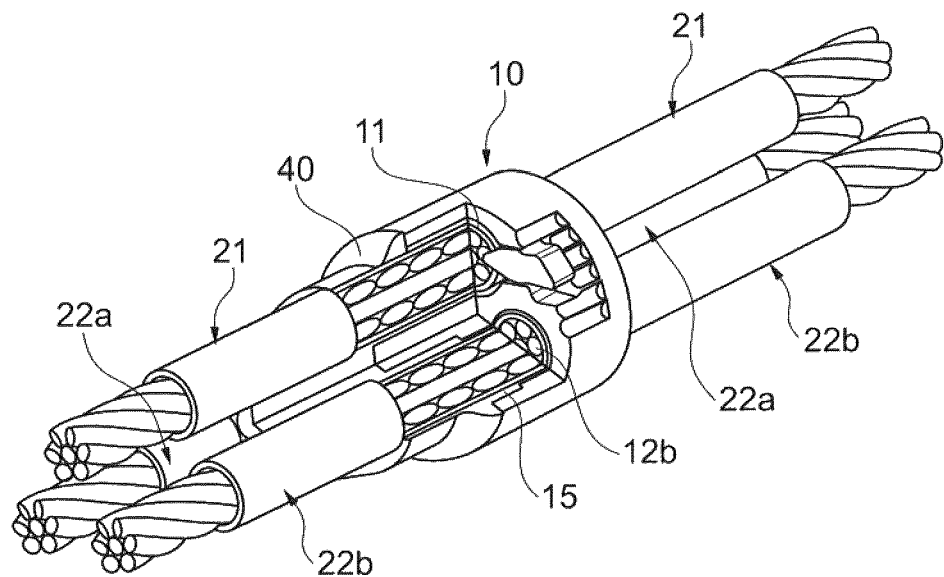
FIG. 9a is a perspective exploded view of a ring with a glue joint.
Figure 9B:
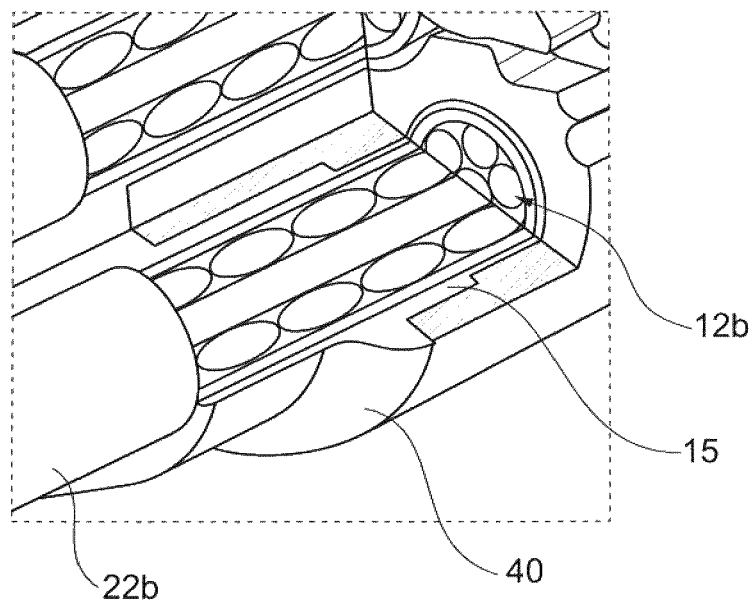

The gradient of stiffness and tightness of the structure can be further improved by the addition of a flexible glue joint 40 at the ends of the ring 10 under the collective sheath, as shown in FIGS. 9a and 9b. This flexible seal 40 is interposed between the edges of the ring 10 and the insulation sheath of the unconnected microcables 22a, 22b, in the area 15 of larger diameter of the electrode crossing lumens 12a, 12b. A polyurethane adhesive may be particularly suitable because of its high fluidity and its ability to migrate in small interstices by simple capillarity.

Figure 13A:
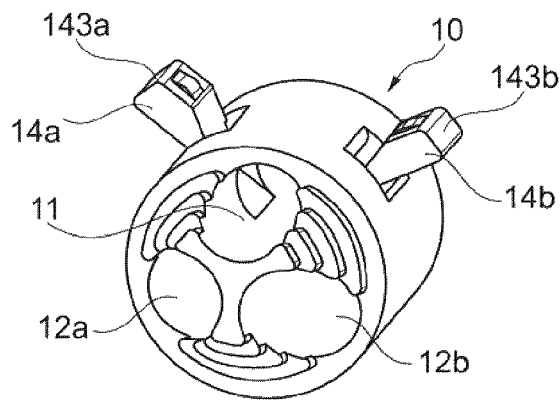
FIGS. 13a to 13c and 14a to 14b illustrate two further respective variants of realization of the metal ring.
Figure 13B:
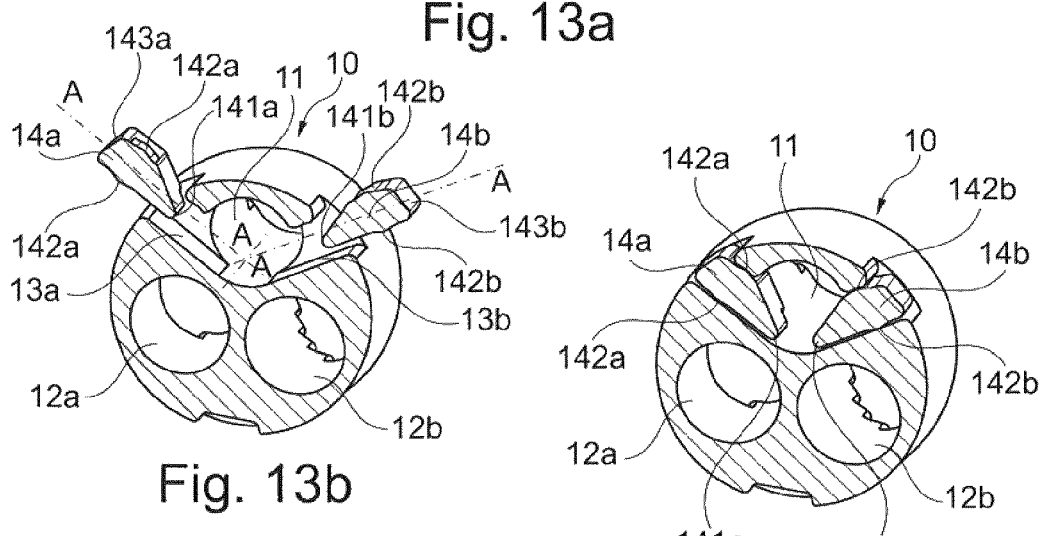
Figure 13C:
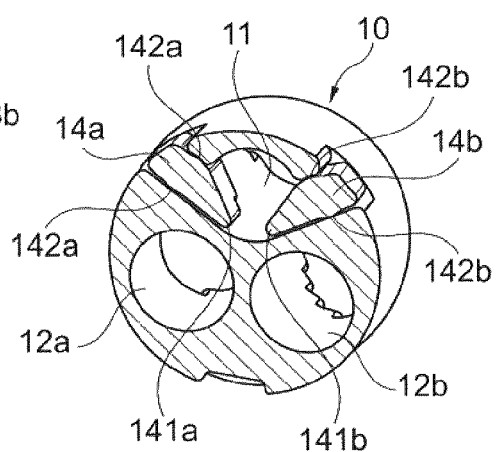
Figure 14A:
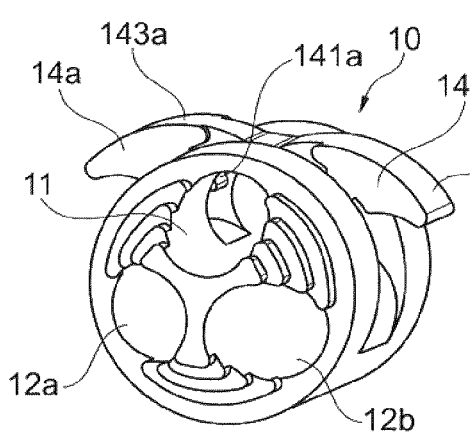
Figure 14B:
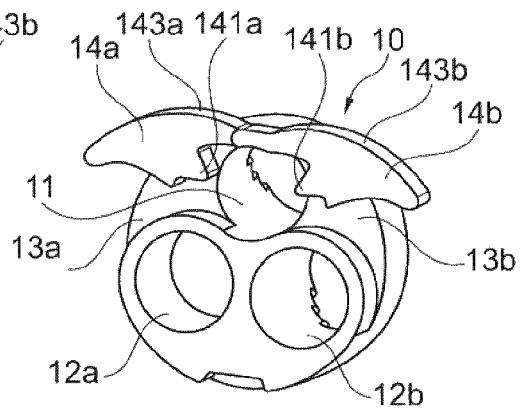

FIGS. 11a to 12b are sectional side views of alternative embodiments of metal rings. The variant of FIG. 11a implements a connection punch 14 cut in the ring 10, capable of perforating the sheath of a microcable disposed within the connection lumen 11 by mastered deformation of the circular structure of the ring without breaking the attachment points of the punch 14 with the ring. The advantage of this variant is the material continuity in the punch/ring electrical connection and the maintaining of optimum sealing. In FIG. 11b, the ring 10 and the member 14' consist of two perforated materials of different rigidities, combined in the same mastering section in order to program the localized deformation of the connection lumen 11. This variant does not require angular tracking during crimping. Variants of FIGS. 11c-12b have elements 14", 14''' of unique mobile connection of the fork type, the benefits of which are double cut of the insulating sheath of the microcable to be connected and a native "pincer" effect. More specifically, the embodiment of FIGS. 12a and 12b includes a connection clipping element 14''' in the connection lumen 11. The embodiment of FIGS. 13a to 13c illustrate an alternative to the translation movement of the drawers 14a, 14b along an axis AA passing through the center of the connection lumen 11. The embodiment of FIGS. 14a-14b illustrates an alternative implementing a rotation of the connection drawers 14a, 14 in their guiding tunnel 13a, 13b.

What is claimed is:

1. A multipolar lead for implantation in a venous, arterial, or lymphatic network, and for use with an electric stimulation or detection device, comprising:
   at least two microcables, each having a central conductor for connection to the electric stimulation or detection device; and
   a first ring having at least two lumens, each sized to receive a microcable of the at least two microcables, wherein one of the at least two lumens is a connection lumen which receives a first microcable of the at least two microcables;
   wherein the first ring further comprises a connection element movable into the connection lumen to pierce a sheath of the first microcable and to press into the central conductor of the first microcable received by the connection lumen, electrically connecting at least a portion of the first ring to the central conductor;
   wherein the connection element is movable through at least one guiding tunnel transverse to the ring, formed between the periphery of the ring and the connection lumen, wherein the connection element slides in the guiding tunnel.

2. The multipolar lead of claim 1, further comprising a second ring having at least two lumens comprising a pass through lumen configured to receive the first microcable and a second connection lumen configured to receive a second microcable of the at least two microcables; wherein the second connection lumen pierces a sheath of the second microcable to electrically connect at least a portion of the second ring to the second microcable.

3. The multipolar lead of claim 2, wherein the first microcable is connected to a first port of the electric stimulation or detection device and wherein the second microcable is connected to a second port of the electric stimulation or detection device.

4. A multipolar lead for detection/stimulation for implantation in a venous, arterial or lymphatic network, comprising:
   at least two microcables, each comprising a full central conductor for connection to a generator of an active implantable medical device, and each having an insulating polymeric material surrounding the central conductor on its periphery and along its length; and
   at least one detection/stimulation electrode for electrically connecting to a central conductor of a microcable and to come against a wall of a target vessel of said venous, arterial or lymphatic network, wherein the at least one electrode comprises a cylindrical metal ring having a longitudinal connection lumen to receive a microcable and to form an electrical connection between at least one portion of the ring and the microcable, and at least one longitudinal lumen for passing the other microcable without forming an electrical connection;
   wherein the at least one electrode further comprises a conductive member for forming the electrical connection by perforation; and
   wherein the ring comprises at least one guiding tunnel transverse to the ring, formed between the periphery of the ring and the lumen for electrical connection, wherein the conductive member slides in the guiding tunnel.

5. The multipolar lead of claim 4, wherein the external diameter of the lead is at most equal to 2 French (0.66 mm).

6. The multipolar lead of claim 4, wherein the conductive member is a drawer having an inner end shaped to penetrate the sheath of the microcable present in the connection lumen in order to make the electrical contact between the ring and the central conductor of the microcable.

7. The multipolar lead of claim 6, wherein the axis (AA) of sliding of the connection drawer passes through the center of the connection lumen.

8. The multipolar lead of claim 7, wherein the ring comprises two opposed connection drawers.

9. The multipolar lead of claim 6, wherein the connection drawer, when in a perforation position, is fully refracted into the guiding tunnel.

10. The multipolar lead of claim 6, wherein the inner end of the connection drawer has a protruding shape.

11. The multipolar lead of claim 6, wherein the connection lumen has a circular opening of a diameter equal to the diameter of the microcable connected to the ring.

12. The multipolar lead of claim 6, wherein said at least one electrode crossing lumen has a circular opening of a diameter greater than the diameter of the microcable not connected to the ring.

13. The multipolar lead of claim 6, comprising, on the periphery of the ring, at least one zone with non-crossing longitudinal grooves, wherein the radius of the longitudinal grooves is at least equal to 5 μm.

14. The multipolar lead of claim 6, wherein said lead is covered with a collective outer sheath comprising a heat-shrinkable insulating material, and wherein windows are provided in the sheath around detection/stimulation surfaces of the ring.

15. The multipolar lead of claim 4, further comprising a seal of flexible adhesive located in the ring ends, wherein the flexible adhesive is made of polyurethane.

16. The multipolar lead of claim 6, wherein at least one of: (a) a chamfer and (b) a recess tangent to the lumens of the ring, is arranged at each end of the ring.

* * * * *